(12) United States Patent
Arnold et al.

(10) Patent No.: US 11,291,362 B2
(45) Date of Patent: Apr. 5, 2022

(54) SYSTEMS AND METHODS FOR EYE EVALUATION AND TREATMENT

(71) Applicants: Robert Wendell Arnold, Anchorage, AK (US); Alex Damarjian, Chicago, IL (US)

(72) Inventors: Robert Wendell Arnold, Anchorage, AK (US); Alex Damarjian, Chicago, IL (US)

( * ) Notice: Subject to any disclaimer, the term of this patent is extended or adjusted under 35 U.S.C. 154(b) by 674 days.

(21) Appl. No.: 16/178,015

(22) Filed: Nov. 1, 2018

(65) Prior Publication Data

US 2019/0125180 A1    May 2, 2019

Related U.S. Application Data

(60) Provisional application No. 62/580,052, filed on Nov. 1, 2017.

(51) Int. Cl.
| | |
|---|---|
| *A61B 13/00* | (2006.01) |
| *A61B 3/00* | (2006.01) |
| *A61B 3/14* | (2006.01) |
| *A61B 3/02* | (2006.01) |
| *A61B 3/032* | (2006.01) |
| *A61B 3/113* | (2006.01) |
| *A61B 3/08* | (2006.01) |

(Continued)

(52) U.S. Cl.
CPC ............ *A61B 3/032* (2013.01); *A61B 3/0033* (2013.01); *A61B 3/0041* (2013.01); *A61B 3/0091* (2013.01); *A61B 3/066* (2013.01); *A61B 3/08* (2013.01); *A61B 3/10* (2013.01); *A61B 3/113* (2013.01)

(58) Field of Classification Search
CPC ....... A61B 3/103; A61B 3/032; A61B 3/1015; A61B 3/0033; A61B 3/107; A61B 3/024; A61B 3/036; A61B 3/0041; A61B 3/14; A61B 3/113; A61B 3/1225; A61B 3/02; A61B 5/16; A61H 5/00; G09B 17/04
USPC ........ 600/558; 351/200, 201, 203, 205, 206, 351/209–211, 221, 222, 237–246
See application file for complete search history.

(56) References Cited

U.S. PATENT DOCUMENTS

| | | | |
|---|---|---|---|
| 7,275,830 B2 * | 10/2007 | Alster | A61B 3/0091 351/223 |
| 2009/0086166 A1 * | 4/2009 | Kanazawa | A61B 3/0325 351/240 |

(Continued)

FOREIGN PATENT DOCUMENTS

| | | |
|---|---|---|
| WO | 2001060233 | 8/2001 |
| WO | 2002039754 | 5/2002 |

OTHER PUBLICATIONS

International Search Report and Written Opinion of the International Searching Authority prepared by the USPTO in connection with PCT/US18/058759, dated Jan. 2, 2019; Entire Document (13 pages).

(Continued)

*Primary Examiner* — Dawayne Pinkney
(74) *Attorney, Agent, or Firm* — K&L Gates LLP (57) ABSTRACT

The present disclosure provides a gaming system including an application that can be implemented using a dynamic testing game, wherein the system does not require glasses, goggles, or any other headwear. The system enables a test subject to be screened and treated for vision dysfunctions while engaging with a dynamic video game.

16 Claims, 4 Drawing Sheets

(51) Int. Cl.
*A61B 3/06* (2006.01)
*A61B 3/10* (2006.01)

(56) References Cited

U.S. PATENT DOCUMENTS

2010/0195051 A1* 8/2010 Murray ................. A61B 3/113
351/209
2013/0002660 A1 1/2013 Chikazawa

OTHER PUBLICATIONS

"Infants perceive two-dimensional shape from horizontal disparity", Infant Behavior and Development, dated Jul. 27, 2018; Entire Document (6 pages).

* cited by examiner

SYSTEMS AND METHODS FOR EYE EVALUATION AND TREATMENT

CROSS-REFERENCE TO RELATED APPLICATIONS

This application incorporates by reference and claims the benefit of priority to U.S. Provisional Application 62/580,052 filed on Nov. 1, 2017.

BACKGROUND OF THE INVENTION

The present subject matter relates generally to systems and methods for assessing and treating human vision.

Typically, vision screening of children is performed manually. This method requires trained personnel to administer the screening. The requirement for trained personnel and expensive, technical testing machines creates a logistical barrier for mass screening. Furthermore, the lack of standardization among different screeners raises concern over accuracy and consistency. Conventional testing of the sensory aspects of the visual system requires a response. Conventionally, a child or adult views an image on a flat plate representing small optotypes (for visual acuity), overlapping varied hues (for color) and overlapping separated right and left off-set images (for depth perception).

It is very difficult to estimate the visual acuity of infants. A method has been devised called "forced preferential looking" wherein an infant, given a presentation of two large cards equal gray (50% white and 50% black stripes) will usually gaze toward the side with widely spaced gratings. Clinically, this is done with an expert technician peering at the infant through a small hole between different paired cards, and seeing if more-than-random infant glances occur at a given level of coarseness of black-white gratings occurs. More cards with finer black-white gratings are then presented to determine a threshold preferential looking as long as the infant can be coaxed into participation. The fine grating correlates with better acuity. Problems with current technology include the need for expert screeners, the binary selection cards (only left-right choice gaze) and the difficulty keeping an infant interested or awake enough to complete the screening.

Some patients have an unstable eye movement disorder called "latent nystagmus" (e.g., fusional maldevelopment nystagmus). When one eye is covered or deviated, the remaining seeing eye does not hold still fixation, but instead experiences horizontal, vertical and torsional nystagmus or jerky movement which degrades the image. Conventionally, in order to accurately test acuity of a nystagmus patient, the non-tested eye must be open and viewing, but partially blurred so the answer is presumed from only the non-blurred eye.

Efficient screening of visual functions would be much more helpful if they could be performed in community screening and as an important aspect of the comprehensive eye examination of children and adults. Young children and children with developmental delays are usually untestable with conventional acuity, stereo and color test methods. The requirement for binocular-image separating goggles makes screening difficult or impossible for children or young adults who are averse to wearing goggles on their faces.

Photographing the eye's red reflex has been proposed as an alternative way of evaluating for vision problems in children. In theory, photoscreening allows testing of very young or developmentally impaired children who could not otherwise cooperate with manual screening techniques. While intriguing, photoscreening does not check the child's vision. Photoscreening can only check for certain eye conditions (e.g., amblyopia risk factors) which may impair vision. In addition, photoscreening requires specialized equipment and training. These limitations make photoscreening less desirable for use with children old enough to read an eye chart. Photoscreening can aid in early vision screening, but it must be followed by sensory testing of acuity with monocularity assured in a sensitive manner when children are older and able to efficiently cooperate with the testing. Furthermore, interpretation on site of results for delivery at the test location is often not accurate. Offsite, professional interpretation improves accuracy but delays result and makes coordinating medical referrals difficult.

Another method to check a child's vision and screen for visual dysfunction such as amblyopia is a professional examination in an eye doctor's office. Although a full examination of presumed high-risk individuals has the potential to be the most thorough method of screening for eye problems, it is not practically performed in the schools. Even if every child could visit an eye doctor's office, the costs would be overwhelming. Furthermore, not all eye doctors are trained the same. Routine exams on all children makes most exams low risk, and therefore, exams become much less sensitive. The lack of a standardized child's eye examination makes even this most expensive proposition subject to accuracy and reliability concerns. It also presents the possibility of over-prescription of eye services.

Leading experts in children's vision all agree that early vision screening is important. While manual screening, photoscreenings, and full eye examinations all have a role to play in detecting visual dysfunction in children, it is obvious the current screenings are failing to efficiently and thoroughly test the near vision of children, much less treat their vision maladies.

Accordingly, there is a need for a vision testing system that is fun and efficient, particularly for children, and wherein the system does not include wearing any glasses or goggles.

BRIEF SUMMARY OF THE INVENTION

The present disclosure provides a vision diagnostic and treatment system and method. Various examples of the systems and methods are provided herein.

The present system provides a gaming platform including an application that can be implemented using a dynamic testing game, wherein the system does not require glasses, goggles, or any other headwear. The system enables a test subject to be screened for vision dysfunctions while engaging with a dynamic video game.

The gaming device and system can be used both for diagnosis and treatment. Eye doctors need to obtain values for near visual acuity, both right and left eyes. Particularly advantageous is the present method that can determine the visual acuity with both eyes open. Further, the present method can be used to diagnose infants that are typically not able to be screened, or must rely on complex forced-preferential looking methods by an expert screener. Once the method obtains a value for near acuity, color, stereo, and preferential looking, further testing can be suggested by the system to be performed to more precisely and accurately define the sensory level for the patient.

An advantage of the present systems is providing accurate, precise, and efficient assessment for determination of near visual acuity (right and left eyes unpatched), near stereo acuity, color vision (right and left eye), and preferential looking (infant, preverbal acuity assessment).

Another advantage of the present system is providing a system to treat amblyopia without forcing the patient to wear an eye patch or dilating the good eye to force the bad eye to strengthen itself. The present method allows a treatment that uses both eyes but provides a binocular treatment that strengthens the weak eye. Similarly, the present system does not require the conventional eye-patch method of strengthening a weaker eye, wherein a patch must be worn many hours each day by children, which is frustrating to the child as well as isolating. The present system can strengthen a weak eye by allowing both eyes to work together in a binocular treatment environment that emphasizes the amblyopic eye while giving less detail to the sound eye.

A further advantage of the present system is providing a non-memorizable testing style, in contrast to conventional eye exams that are not only static but memorizable.

Another advantage of the present system is providing a method of vision diagnosis and treatment for children and people with mental disabilities (e.g., autism, downs syndrome, etc.).

Another advantage of the system is the ability to present a visual acuity optotype to the desired tested eye separated from the non-tested eye by virtue of the split-pixel screen so both eyes can be open, steadier, in patients with nystagmus.

Another advantage of the present system is providing a test that can be used repetitively to assess and monitor progressive conditions like concussions, multiple sclerosis, hydrocephalus, diabetes, toxic substance exposure, optic nerve disorders, among others.

Another advantage of the present system is providing a multi-use, child-friendly form of binocular amblyopia therapy.

Yet another advantage of the present system is providing a diagnosis and treatment in a game format that can include games that are child-friendly and educational while simultaneously diagnosing and treating eye conditions. In an example, an animated figure can be displayed as a reward for the child to indicate correct choices.

Another advantage of the present system is providing a game format that can be used on conventional gaming technology, e.g., Nintendo™ 3DS, among others.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

The present disclosure provides systems for visual assessment that engage a test subject in a familiar video game format. As used herein, the computer system, regardless of the operating system that it uses or its source of design or manufacture, has a data input means such as a keyboard and/or touch screen, including a monitor having a screen for displaying alphanumeric and graphic images. A child's natural desire to play games encourages and insures the child's participation. During the course of game play, the system automatically assesses for visual acuity, stereopsis, binocularity, game alignment, and if appropriate color vision. In an example, a race car video game is selected to provide the testing motif to maximize the child's interest and participation. The particular game chosen to encourage the child's cooperation may vary; however, the game can be standardized so that the same presentation is provided to all of the students and that variations in the test results do not result from the chosen game. It is important to note that no formalized training should be required of the administrator or proctor to administer the test.

The present method eliminates variations in the training of proctors and provides a system wherein the test may be administered by anyone, even with the most rudimentary of computer skills. The need to train large number of volunteers to perform vision screening is therefore unnecessary. The simplified logistics of vision screening with this method allow children to be tested at any time of any day and previously disrupting influences, such as school absences or late-year transfers, will not affect the test results nor will it result in a missed screening.

The method of the present invention provides a test that can be completely standardized from child to child independent of when or where it is performed and permits automated standardized nationwide testing and collection of data to permit analysis and evaluation. The present system can be administered using computer technology widely available at schools throughout the United States and elsewhere. Testing paradigms can be based on accepted vision assessment protocols to ensure accuracy, and/or based on personalized assessment criteria.

The motor skills required by the test subject can be monitored during game play and test presentations can be dynamically adjusted by the system to eliminate inattention or motor skill difficulties as sources of inaccuracy. An additional element of the present system is the provision for the storage and collation of data locally and in a remote centralized database. As such, the system can automatically track the success of vision screening programs. Customized reporting can be provided for epidemiological studies and can be tailored to virtually any specific request.

Once the test subject fairly understands the purpose and goals of the game, the system proceeds with the administration of appropriate tests for screening visual acuity, stereopsis, binocularity, eye alignment and color vision (if appropriate). The test can be carefully chosen to be readily comprehensible by pre-literate and school-age test subjects. A video game format has been found to be most attractive since it can be inherently interesting (and thus incorporates incentives to learn and understand the test). The game can be simple but interesting and present a readily acceptable challenge to the test subject while rewarding performance by audio or visual presentations. Most importantly, the test can provide consistently objective results to permit data correlation among test results of many test subjects.

The system can include a plurality of games that can be chosen from dependent on the age and mental capacity of the test subject. For example, the game can be a race car that is viewed on the user interface traveling a simple multi-lane road. However, any number of other game formats may be used. It is important that the method of the present invention engage the test subject child with a non-threatening environment further, the cognitive skill required must be age appropriate to ensure comprehension. Further, the motor skill required to interact with the test game must be age appropriate. Thus, the system determines the suitable game based on the supplied data entered into the database.

A component of vision is represented by the occipital lobe of the brain, must be learned over the course of the first decade of a human's life. Four important components include central visual acuity, peripheral awareness, color vision, and binocular vision/stereopsis are accessed to determine whether a test subject has clear images in each eye that are also aligned on objects of interest. The system enables a pediatric ophthalmologist to accurately and precisely measure visual function and apply therapy to improve visual function.

Visual acuity is the ability to resolve small objects primarily using central, macular vision at a given near or far distance. Stereo acuity is the ability to perceive depth perception, or virtual depth perception, when horizontally disparate images are shown to both eyes simultaneously. Amblyopia is a disruption in normal brain learning of vision during a child's first decade due to refractive error in one or both eyes, strabismus (i.e., constantly misaligned eyes), or deprivation of images cause by childhood cataract. Nystagmus is rhythmic involuntary movement of the eyes.

The system can include a visual acuity test, a binocularity test, amblyopia diagnosis, eye alignment, and color test. It is contemplated the tests are performed concomitantly and/or separately. For example, the visual acuity test results can be an indication that both eyes are 20/20 or better. The results of the binocularity test can indicate that the child is suppressing one eye and/or double vision. The system can monitor head and eye movement improving image size and location presentation as well as monitoring performance of sensory testing or amblyopia therapy. The eye alignment test can be conducted to determine the alignment of the eyes. For example, the system can include a binocular game for amblyopia therapy that includes presenting different, related complementary images to both eyes in an attempt to treat the amblyopia in the "bad" eye, while preserving acuity in the sound eye, and improving binocular vision.

Specifically, the system 10 can include a device 12 that includes a monitor screen (e.g., user interface 14), a touch screen 16 that can be used for user selection. The system can present a unique image to the right eye separated from the images viewed by the left eye, because each pixel of the screen is actually two separate pixels uniquely viewed from the right and left side. The system can be a three-dimensional system that includes a camera that monitors the head, face, and/or eye movements of the subject and can adjust screen presentation accordingly. The system can include a sensory testing game for visual acuity, stereo acuity, and color vision using dynamic presentation on the three-dimensional video screen. The system can include entertainment games, educational games, or combinations thereof. The content of the games can be viewed by the amblyopic eye, enabling patients to improve amblyopia, curing otherwise permanent blindness by interacting binocularly with a virtually three-dimensional game.

In an example, the game can include a plurality of shapes (independently chosen from any shape, including, but not limited to circles, squares, rectangles, triangles, asymmetric shapes, animals, objects, etc.) having different colors, depth, and acuity. The shapes can be organized and utilized in various games or tasks.

Figure 1:
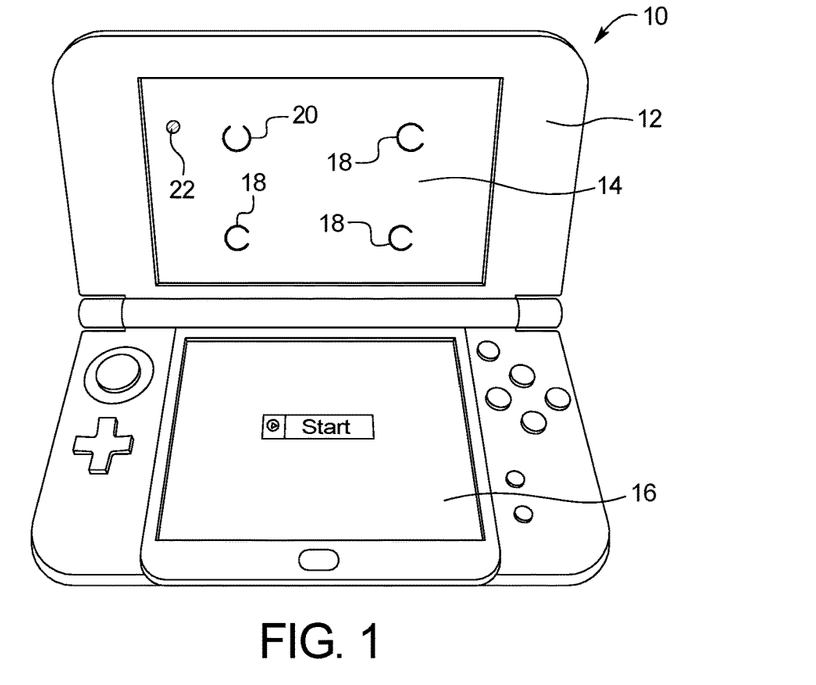
FIG. 1 is an example of a gaming platform (e.g., Nintendo 3DS™) image illustrating "C" optotype, monocular near acuity screening with patient making lower touch-screen selection of the randomly presented rotated "C" that looks like a "U" in one quadrant of the upper binocular screen.

In an example, the system 10 can include an acuity test that displays four shapes, wherein three are identical shapes 18 and one is a dissimilar shape 20, wherein the dissimilar shape 20 may only be slightly different from that of the identical shapes 18. As shown in FIG. 1, the three identical shapes 18 are "C"s and the dissimilar shape 20 is a "U". The use is instructed to select the dissimilar shape. If the user selects the "U", then the selection is correct and the acuity score is updated accordingly. If the user selects one of the three "C"s, then the selection is incorrect. In an example, in the case of an incorrect selection, a child-friendly figure of a soccer referee with a yellow card and "Try Again" can be briefly shown on the user interface, the acuity score is updated accordingly, and the patient can restart the test.

Figure 2:
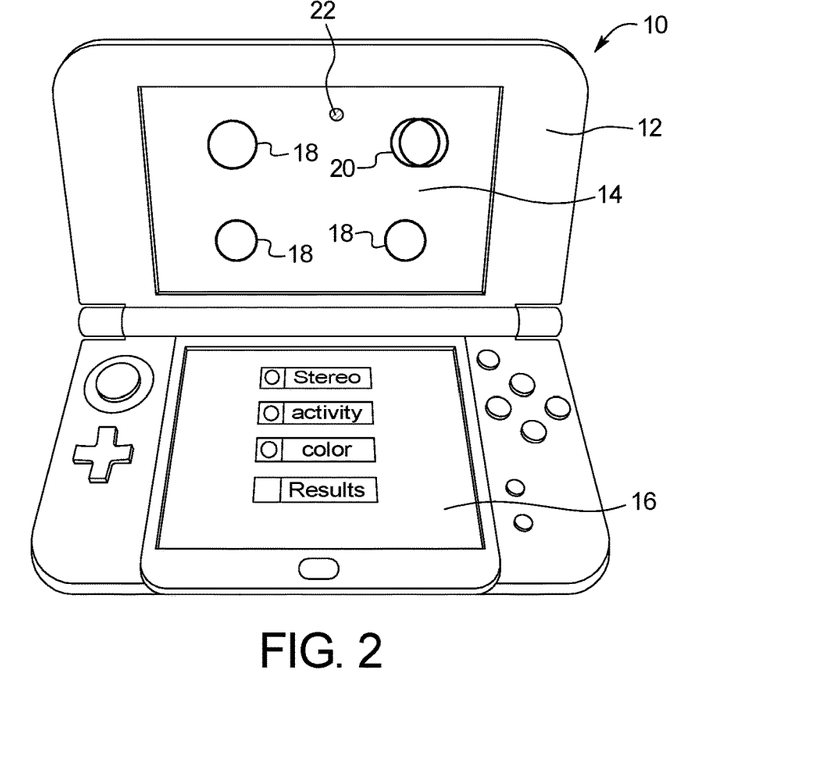
FIG. 2. Is an example of a gaming platform illustrating a near vision test selection menu on lower touch-screen and superimposed binocular stereo presentation on the upper 3-D screen.

An example of stereo testing is shown in FIG. 2. For example, the display can include four identical shapes, wherein at least one of the shapes is in three-dimensions (i.e., dissimilar shape 20). The user can use the cursor to select which of the shapes is in three-dimensions. Based on the user selection, the system can generate a stereo score.

Figure 3:
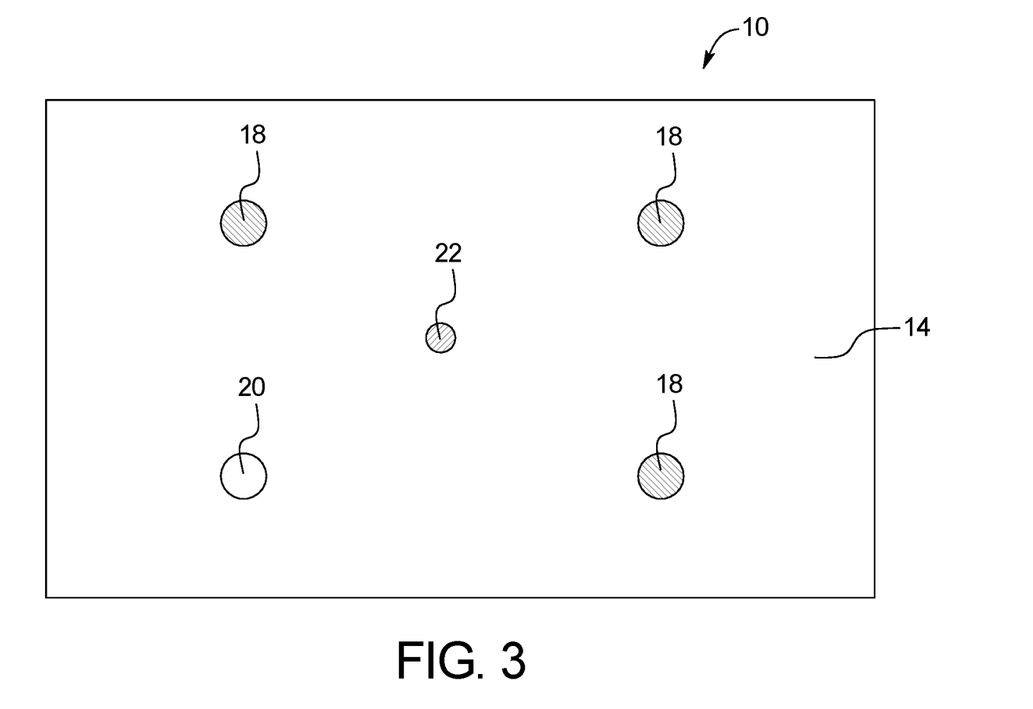
FIG. 3 is an example of an upper screen image illustration color vision testing with one colored disc randomly selected to vary the hue.

In an example, the color test can include four shapes (e.g., any shape, such as animals, plants, objects, text, cartoon figures, etc.), wherein each shape can be the same color. One of the circles can change into a different color, as shown in FIG. 3, wherein the test subject is instructed to identify, via touch screen or controllers, the circle that has changed (i.e., the dissimilar shape 20). During the testing, the system can track the movement of the eyes of the test subject for monitoring testing reliability.

In an example, the shapes can include at least four circles that are green (i.e., identical shapes 18) and one of the shapes morphs into yellow (i.e., the dissimilar shape 20), wherein the user is directed to select the dissimilar shape and/or color from the initial four identical shapes 18 (e.g., letter "C"). In an example, one of the four circles can morph into a different shape, such as a "U", wherein the user identifies which shape has changed (i.e., the dissimilar shape 20). The selection and time of selection of the correct morphed shape can determine a score for visual acuity. For example, not only does the correct selection of the dissimilar shape 20 contribute to the score, but the time it takes for the user to select the correct shape once it morphed into the dissimilar shape 20 can also be included in the score. The user can select the dissimilar shape 20 by any mechanism, including, but not limited to, moving a cursor 22 on the displayed screen 14 via a touch pad 16 on the device 12.

Figure 4:
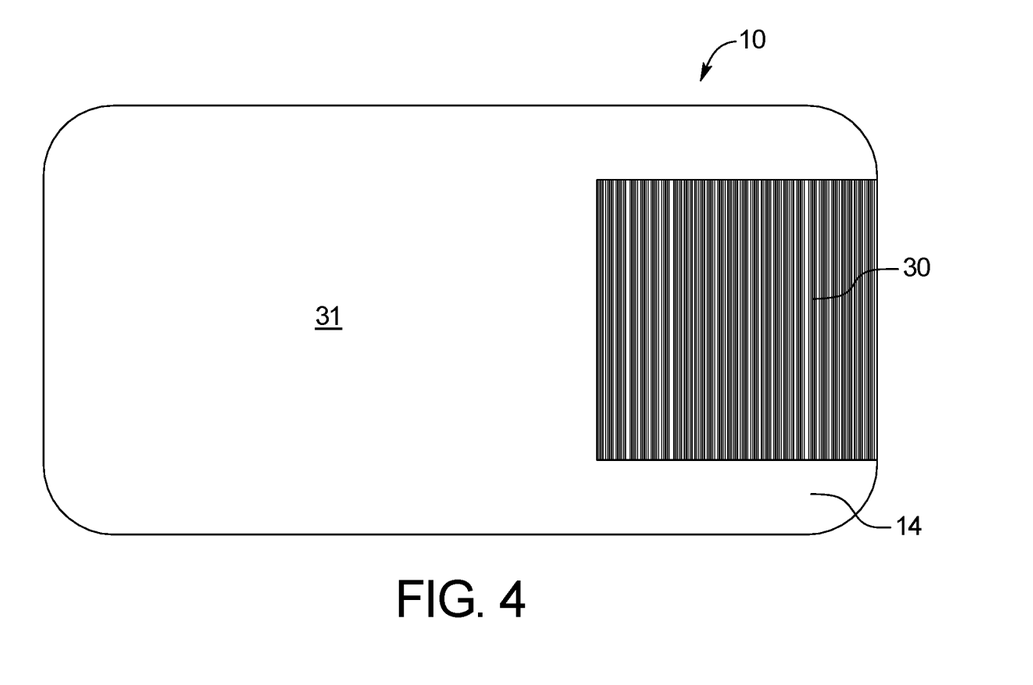
FIG. 4 is an example of a screen shot illustrating forced preferential looking presentation.
Figure 5:
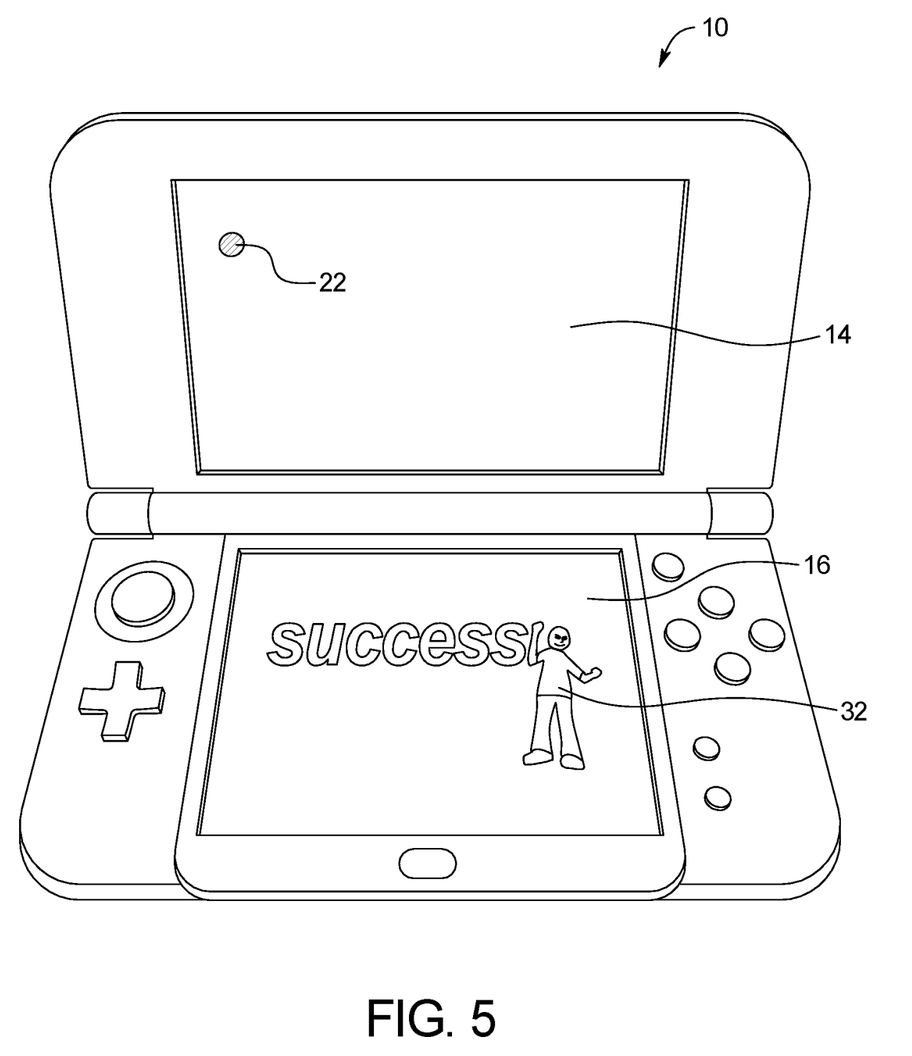
FIG. 5 is a schematic of a reward animation for correct selections.

The system 10 can include a forced preferential looking test. An example of a displayed screen for the preferential test is shown in FIG. 4. Forced Preferential Looking is based on the observation that a pre-literate child will rapidly switch gaze toward a coarser pattern 30 of equally-gray lines and away from a uniformly gray region 31. The system 10 can generate randomly alternating right or left screen areas with coarse, medium and fine gratings, the degree of coarseness relating to poorer vision. Region 30 in FIG. 4 is an example of a fine pattern of gratings toward which the child should rapidly fixate. The system can include an eye and face tracking capability to facilitate scoring of forced preferential looking. In an example, the eye and face tracking capabilities can be provided via a Nintendo 3DS™.

Further, the system 10 can also arrange the shapes 18, 20 in such a way that the system trains the weaker eye via the brain of the user to strengthen. Typically, children with one weaker eye are forced to wear an eye patch over the stronger (sound) eye to train the weaker eye to not rely on the stronger eye but instead strengthen itself. However, wearing an eye patch is not only inconvenient, but also socially isolating. Therefore, the system can strengthen the weaker eye in a fun and entertaining way, which is advantageous. The system can be used to present information (e.g., images, shapes, colors, etc.) separately to the right and left eye. Any movie, or ideally an educational game can be presented with the majority of visual information (clarity, brilliance, contrast, portions of the view) shown to the amblyopic (i.e., bad) eye and a lower visual information (dimmer, blurred, less contrast, lacking specific details) shown to the non-amblyopic (i.e., sound, good) eye.

Although, it is contemplated that any game format can be used. For example, the system 10 can include a race car, chess game, checkers game, sports, basketball game, bowling, among others. For example, a car can be positioned within four possible lanes, wherein movement of the car can be identified by the test subject to determine the visual assessment. The system can include audible and/or visual instructions for the object of the game including the rules and how to win.

In an example, random dots can be used, which create no distinguishable pattern if presented to only one eye or the other. However, when presented to both eyes simultaneously, a three-dimensional image is created. In a manner analogous to color vision and visual acuity testing, this three-dimensional image can be displayed as or associated with at least one of the presented shapes on the user interface. In an example, the three-dimensional image can be in the form of a different shape, such that the test subject can select the circle with the unique three-dimensional different shape from the remaining circles without an associated three-dimensional shape. Children without adequate stereopsis will be unable to discern the three-dimensional image presented on the shape.

In the stereopsis phase, identical images can be displayed in each quadrant of the upper screen, wherein after a predetermined amount of time one of the images in one randomly selected quadrant becomes visible to either the left or the right eye independently to confirm comprehension. The correct shape choice by the user will be invisible to children without adequate stereopsis (only dots will be visible) and will result in random shape selection (e.g., circle selection, lane selection in the case of the car game, etc.). The appearance of one of the objects in the randomly selected target quadrant can appear to levitate off the screen because the right eye screen image is shifted to the left and the left eye screen image of that object is shifted to the right (e.g., as shown as object 20 in FIG. 2) Results of stereopsis testing can be generated and displayed automatically at the end of the vision assessment evaluation.

Figure 6:
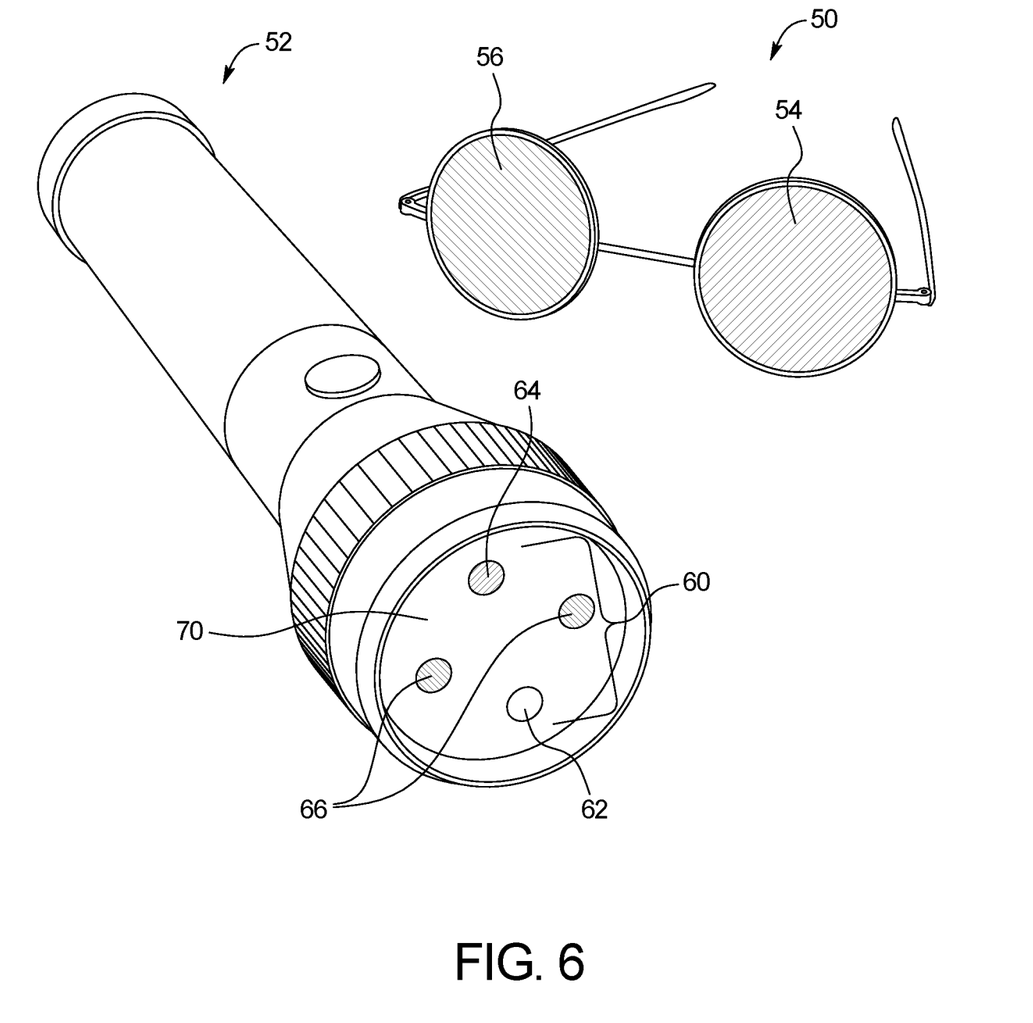
FIG. 6 is an example of a schematic of the system including a handheld flashlight apparatus and spectacles.

In an example, a Worth-Dot test is conducted by presenting a screen associated with at least four dots 60, wherein the four dots include at least one illuminated circle with a white dot pattern 62, and by showing one illuminated red dot 64 and two illuminated green dots 66 viewed with spectacles 50 having one red lens 54 and one green lens 56. The system 10 can determine whether normal binocularity, right eye suppression, left eye suppression or double vision exists by which of the four possible shapes 60 is selected by the user being test. If the test subject chooses the circle with two red dots 64, then left eye suppression exists; if the test subject chooses the circle represented by three green dots, then right eye suppression exists. Similarly, a circle choice corresponding to the four dots in the three-dimensional image indicates normal binocularity while the choice of the circle corresponding to the three-dimensional image is indicative of double vision. The dots 60 can be illustrated on the user interface 14 of the system. In an example, illustrated in FIG. 6, the dots 60 can be illustrated on a separate hand-held flashlight apparatus 52 including a display cover 70 displaying the at least four dots 60. The spectacles 50 can be used in combination with the device 12 and/or the handheld flashlight apparatus 52. In an example, the user can make a selection using the user interface 14 of the device 12 while viewing the handheld apparatus 52 with the spectacles 50.

If the test indicates the test subject is suppressing one eye, amblyopia may be diagnosed. The system can provide an amblyopia treatment game. The treatment game can force the weaker eye of the test subject to work in order to excel at the game. As a result, the test subject can heal the brain to the weaker eye in a fun method without the use of eye patches or additional equipment.

In an example, eye alignment can be evaluated using the principle of a troposcope, wherein separate images are presented to each eye and then measures whether a realignment response is necessary to bring the two images together. For example, the test may include two or more circles, wherein the test subject is instructed to move, via the user interface, at least one of the first circles to align with a second circle. The first circle may be visible to only one eye of the test subject and the second circle may be only visible to the opposite eye. If the eyes are well aligned, the first circle and second circle can be aligned by the test subject. If the eyes are not well aligned, the circles not be superimposed properly by the test subject. What appears to the test subject as proper positioning of the second circle with the first circle will actually result is the first circle being placed in line with the second circle or super imposed on the first circle. It is possible to determine both the direction of the eye misalignment (esodeviation or exodeviation) as well as the approximate degree of eye misalignment based on the working distance from the user interface and the distance the first circle and second circle are misaligned.

Not only does the present system include the test subject's responses to determine the visual assessment, but the system can also include external objective assessment of the visual capabilities of the test subject. For example, the present system can include an eye tracking device included in the testing device or external from the testing device, wherein the testing device includes a user interface to present the testing game to a testing subject. The tracking device includes an eye tracker for tracking movement of at least one of patient's eyes to determine a gaze point and its position in three-dimension without requiring the testing subject to wear any tracking equipment or restricting head movement.

The tracking system can include monitoring saccadic eye movement, wherein the system is able to detect changes in eye gaze position during the assessment testing. For example, during the visual acuity test, a binocularity test, and/or an eye alignment test, the tracking system can be simultaneously monitoring the eye movement of the test subject while the test subject is engaging with the game via the user interface.

In an example, the eye tracking system provided by Tobii is used, which in an example has a head position tolerance of 30×15×20 cm and is able to detect the distance of a child's eyes from the eye tracker and the position of the eyes in the camera field of view, thereby allowing for the calculation of the three-dimensional position of the eyes from a current fixation point. The system can calculate where stimuli are displayed on the user interface during the testing game for assessing any particular visual field angle. The device does not need positional calibration, so the child is free to move around within the field of detection. Also, the system provides good gaze data accuracy and the ability to detect the very fast movements of the eye in real time and does not require the subject to wear any equipment on their head. In an example, with or without the gaming system, the eye tracker has no moving parts and as such is highly unobtrusive, which is of importance as children can be easily distracted.

A one-eyed patient may be able to see the screen intended for the right eye, then move the head to the left and therefore "see" the left eye screen. The head movement tracking of the system would detect this patient "peeking," and update the results accordingly.

In order to allow the calculation of the appropriate screen position for any particular visual field point being assessed, the position of each eye in three-dimensional space relative to the display screen must be known. The Tobii eye tracker provides real time data giving the distance of each eye from the eye tracker camera and the position of each eye in the camera field of view. The real-time calculation of the three-dimensional position of each eye relative to any point on the display screen provides a way of determining the correct size and position of the stimuli to be presented on the screen at any moment for any particular visual field point being assessed.

The response of a subject's eye gaze is monitored when stimuli (e.g., various shapes) are shown in different positions on the display screen corresponding to different points in a subject's visual field. An algorithm is used to decide whether the test subject is able to see the new stimulus based on the direction and length of movement of eye gaze and the timing of that movement. If a test subject sees something in their peripheral vision the natural response is to gaze at it. If the point is not seen there could be no change in eye gaze position or a searching eye gaze movement. The algorithm automatically distinguishes these responses in real time based on the direction and angular length of any fixation change made immediately following the presentation of a new visual field point stimulus, and the timing of any such fixation change. The vector change in fixation point is compared directly with the vector change in the screen position of the stimuli to decide if the subject was able to see the stimuli or not. When the stimulus is displayed, the eye tracker captures eye gaze data in order to verify whether the patient is indeed gazing at the stimulus. In the event that the gaze data suggests that the patient is not fixating on the correct point, further gaze data is captured. This is repeated until the system is confident that the patient is looking at the central stimulus.

The system can generate a report that provides the test results including the assessment of color vision, visual acuity, stereopsis, and binocularity. In the event that the screening results suggest that the student should be referred to an eye care professional, a message to that affect will be prominently displayed in the report her with the possibility of suggested conveniently local eye professionals.

As mentioned above, aspects of the systems and methods described herein are controlled by one or more controllers. The one or more controllers may be adapted to run a variety of application programs, access and store data, including accessing and storing data in the associated databases, and enable one or more interactions as described herein. Typically, the controller is implemented by one or more programmable data processing devices. The hardware elements, operating systems, and programming languages of such devices are conventional in nature, and it is presumed that those skilled in the art are adequately familiar therewith.

For example, the one or more controllers may be a PC based implementation of a central control processing system utilizing a central processing unit (CPU), memory and an interconnect bus. The CPU may contain a single microprocessor, or it may contain a plurality of microprocessors for configuring the CPU as a multi-processor system. The memory may include a main memory, such as a dynamic random access memory (DRAM) and cache, as well as a read only memory, such as a PROM, EPROM, FLASH-EPROM, or the like. The system may also include any form of volatile or non-volatile memory. In operation, the memory stores at least portions of instructions for execution by the CPU and data for processing in accord with the executed instructions.

The one or more controllers may also include one or more input/output interfaces for communications with one or more processing systems. Although not shown, one or more such interfaces may enable communications via a network, e.g., to enable sending and receiving instructions electronically. The communication links may be wired or wireless.

The one or more controllers may further include appropriate input/output ports for interconnection with one or more output mechanisms (e.g., monitors, printers, touchscreens, motion-sensing input devices, etc.) and one or more input mechanisms (e.g., keyboards, mice, voice, touchscreens, bioelectric devices, magnetic readers, RFID readers, barcode readers, motion-sensing input devices, etc.) serving as one or more user interfaces for the controller. For example, the one or more controllers may include a graphics subsystem to drive the output mechanism. The links of the peripherals to the system may be wired connections or use wireless communications.

Although summarized above as a PC-type implementation, those skilled in the art will recognize that the one or more controllers also encompasses systems such as host computers, servers, workstations, network terminals, and the like. Further one or more controllers may be embodied in a device, such as a mobile electronic device, like a smartphone or tablet computer. In fact, the use of the term controller is intended to represent a broad category of components that are well known in the art.

Hence aspects of the systems and methods provided herein encompass hardware and software for controlling the relevant functions. Software may take the form of code or executable instructions for causing a controller or other programmable equipment to perform the relevant steps, where the code or instructions are carried by or otherwise embodied in a medium readable by the controller or other machine. Instructions or code for implementing such operations may be in the form of computer instruction in any form (e.g., source code, object code, interpreted code, etc.) stored in or carried by any tangible readable medium.

As used herein, terms such as computer or machine "readable medium" refer to any medium that participates in providing instructions to a processor for execution. Such a medium may take many forms. Non-volatile storage media include, for example, optical or magnetic disks, such as any of the storage devices in any computer(s) shown in the drawings. Volatile storage media include dynamic memory, such as the memory of such a computer platform. Common forms of computer-readable media therefore include for example: a floppy disk, a flexible disk, hard disk, magnetic tape, any other magnetic medium, a CD-ROM, DVD, any other optical medium, punch cards paper tape, any other physical medium with patterns of holes, a RAM, a PROM and EPROM, a FLASH-EPROM, any other memory chip or cartridge, or any other medium from which a controller can read programming code and/or data. Many of these forms of computer readable media may be involved in carrying one or more sequences of one or more instructions to a processor for execution.

It should be noted that various changes and modifications to the embodiments described herein will be apparent to those skilled in the art. Such changes and modifications may be made without departing from the spirit and scope of the present invention and without diminishing its attendant advantages. For example, various embodiments of the systems and methods may be provided based on various combinations of the features and functions from the subject matter provided herein.

We claim:

1. A system for determining visual dysfunction of a test subject, the system comprising:
a screen configured to display image data, wherein each image data includes a first image data component viewable from a first angle and a second image data component viewable from a second angle, wherein the first image data component is different than the second image data component;
a controller; and
a memory coupled to the controller, wherein the memory is configured to store program instructions executable by the controller;
wherein in response to executing the program instructions, the controller is configured to:
display image data on the screen such that, when the test subject holds the screen, the first image data component is only viewable by a right eye of the test subject while the second image data component is only viewable by a left eye of the test subject,
receive user input from the test subject in response to the displayed image data presented on the screen, and
determine vision testing results based on the user input from the test subject, wherein the vision testing results include an acuity score.

2. The system of claim 1, wherein the controller is configured to obtain tracked movement data, via an eye tracker in communication with the controller, for at least one eye of the test subject to determine an eye position in three dimensions without requiring the test subject to wear any tracking equipment, wherein the vision testing results are based on the tracked movement data.

3. The system of claim 1, wherein the image is three-dimensional.

4. The system of claim 3, wherein the three-dimensional image can only be seen by the test subject with adequate visual acuity.

5. The system of claim 1, further comprising a device including the screen, the controller, and an eye tracker.

6. The system of claim 1, wherein the vision testing results include a stereopsis score.

7. The system of claim 1, wherein the vision testing results include a binocularity score.

8. The system of claim 1, wherein the vision testing results include a monocular color vision score.

9. The system of claim 1, wherein the vision testing results include a monocular visual acuity score.

10. The system of claim 1, wherein the controller is configured to present the image data in a format of an interactive video game.

11. A system for determining visual dysfunction of a test subject, the system comprising:
a screen configured to display image data, wherein each image data includes a first image data component viewable from a first angle and a second image data component viewable from a second angle, wherein the first image data component is different than the second image data component;
a controller; and
a memory coupled to the controller, wherein the memory is configured to store program instructions executable by the controller;
wherein in response to executing the program instructions, the controller is configured to:
display image data on the screen such that, when the test subject holds the screen, the first image data component is only viewable by a right eye of the test subject while the second image data component is only viewable by a left eye of the test subject,
receive acuity user input from the test subject in response to the image presented on the screen, wherein the user input from the test subject includes one of a response time, color selection data, and binocularity selection data,
determine vision testing results based on the user input from the test subject, wherein the vision testing results include one of an acuity score, a color score, and a binocularity score based on the one of the response time, the color selection data, and the binocularity selection data of the user input.

12. The system of claim 11, wherein the image is three-dimensional.

13. The system of claim 12, wherein the three-dimensional image can only be seen by the test subject with adequate visual acuity.

14. The system of claim 11, further comprising a device including the screen, the controller, and an eye tracker.

15. The system of claim 11, wherein the vision testing results include a stereopsis score.

16. The system of claim 11, wherein the vision testing results include a monocular visual acuity score.

* * * * *